United States Patent
Wohlschlager et al.

(10) Patent No.: US 9,107,584 B2
(45) Date of Patent: Aug. 18, 2015

(54) METHOD OF REDUCING ULTRASOUND SIGNAL AMBIGUITY DURING FETAL MONITORING

(75) Inventors: Markus Wohlschlager, Sindelfingen (DE); Christoph Franck, Sindelfingen (DE)

(73) Assignee: Koninklijke Philips N.V., Eindhoven (NL)

( * ) Notice: Subject to any disclaimer, the term of this patent is extended or adjusted under 35 U.S.C. 154(b) by 101 days.

(21) Appl. No.: 13/812,151

(22) PCT Filed: Jul. 29, 2011

(86) PCT No.: PCT/IB2011/053380
§ 371 (c)(1),
(2), (4) Date: Jan. 25, 2013

(87) PCT Pub. No.: WO2012/017364
PCT Pub. Date: Feb. 9, 2012

(65) Prior Publication Data
US 2013/0123637 A1    May 16, 2013

(30) Foreign Application Priority Data

Aug. 2, 2010 (EP) .................................... 10171541

(51) Int. Cl.
*A61B 8/02* (2006.01)
*A61B 8/08* (2006.01)
*G01S 7/526* (2006.01)

(52) U.S. Cl.
CPC ................. *A61B 8/02* (2013.01); *A61B 8/0866* (2013.01); *G01S 7/526* (2013.01)

(58) Field of Classification Search
CPC .......... A61B 8/02; A61B 8/0866; G01S 7/526
USPC ........................... 600/407, 438, 453, 455, 483
See application file for complete search history.

(56) References Cited

U.S. PATENT DOCUMENTS

| | | |
|---|---|---|
| 3,910,259 A | 10/1975 | Sullivan |
| 3,991,365 A | 11/1976 | Takeuchi |
| 4,052,896 A * | 10/1977 | Lee et al. .................... 73/861.29 |
| 4,143,650 A * | 3/1979 | Hatke ............................ 600/453 |
| 4,403,184 A | 9/1983 | Witt et al. |
| 4,569,356 A | 2/1986 | Kyozuka |
| 4,573,479 A | 3/1986 | Tuccillo |
| 4,781,200 A * | 11/1988 | Baker ............................ 600/483 |
| 4,984,576 A | 1/1991 | Schulenberg et al. |
| 5,097,837 A * | 3/1992 | Reuschel ...................... 600/453 |

(Continued)

FOREIGN PATENT DOCUMENTS

| | | |
|---|---|---|
| EP | 0359839 A1 | 3/1990 |
| GB | 2220487 A | 1/1990 |

OTHER PUBLICATIONS

Neilson, Jr., D. R., et al.; Signal ambiguity resulting in unexpected outcome with external fetal heart rate monitoring; Jun. 2008; American Journal of Obstetrics & Gynecology; pp. 717-724.

*Primary Examiner* — Baisakhi Roy (57) ABSTRACT

The present invention relates to a method and a device for fetal cardiac monitoring. For improving ultrasonic monitoring, the number of periodic signals, such as signals caused by the fetus and the mother, is assessed and the time window of the signal demodulation is adapted if more than one periodic signal is assessed.

14 Claims, 5 Drawing Sheets

(56) References Cited

U.S. PATENT DOCUMENTS

| | | |
|---|---|---|
| 5,170,791 A | 12/1992 | Boos et al. |
| 5,749,831 A * | 5/1998 | Baker .......................... 600/301 |
| 2005/0251044 A1 | 11/2005 | Hoctor et al. |
| 2008/0161689 A1 * | 7/2008 | Pandit .......................... 600/438 |
| 2008/0188752 A1 * | 8/2008 | Randall et al. ................ 600/455 |
| 2008/0208057 A1 * | 8/2008 | Hoctor et al. ................. 600/453 |
| 2011/0172540 A1 * | 7/2011 | Jackson ........................ 600/453 |

* cited by examiner

METHOD OF REDUCING ULTRASOUND SIGNAL AMBIGUITY DURING FETAL MONITORING

FIELD OF THE INVENTION

The invention relates to the field of fetal cardiac monitoring methods and devices.

BACKGROUND OF THE INVENTION

Electronic fetal monitors or Cardio-Toco-Graphs (CTGs) normally consist of a base unit having a thermal printer, a display and multiple sensor elements for measuring vital parameters, such as uterine activity and fetal heartbeat.

Today's fetal monitors use ultrasound Doppler technology for non-invasive acquisition and recording of the fetal heart rate during gestation and labor. As the mechanical contraction of the fetal heart muscle leads to periodic signal patterns in the ultrasound reflection, the period of the patterns is used by fetal monitors to determine the fetal heart rate. U.S. Pat. No. 4,984,576 describes such a device.

SUMMARY OF THE INVENTION

It is an object of the invention to provide an improved method and device for fetal cardiac monitoring.

This object is achieved by a method of fetal cardiac monitoring, comprising the steps of:
a) receiving an ultrasound signal reflected by a fetus;
b) demodulating the signal received in at least one time window with a specific duration (also called demodulation time window);
c) assessing whether at least one time window contains more than one periodic signal; and
d) adapting the duration of at least one time window in the case of more than one assessed periodic signal;
wherein steps a) to d) are repeated with the adapted or non-adapted time window(s).

The invention is based upon the basic idea that the position and length of the ultrasonic detection volume is determined by the time window during which the reflected signals are received or rather demodulated. The duration of the receive/demodulation time window and the length of the detection volume from which the reflected signals are received are directly proportional. By adapting the duration of the window time, the range of reach can be controlled. A time window with a short duration results in a short detection length and a time window with a long duration results in a long detection length. Normally the duration of the time window is designed to cover a depth range of about 5 cm to about 20 cm. The fetal heart is located at a distance of typically about 10 cm to about 15 cm from the surface of the transducer. In order to cover a wide variety of body measurements an appropriate safety margin is added.

However, all periodic movements of structures inside the ultrasonic detection volume can generate a heart rate within the fetal monitor. It turned out that especially pulsations of the abdominal arteries of the mother cause problems, so that the signal containing information about the fetal heartbeat only represents one portion of the entire received ultrasound signal. Signal contributions from separately moving structures, like maternal or fetal arteries or the umbilical cord, in particular lying behind the fetal heart, are superimposed and actually unwanted, since any signal contribution other than the reflection from the fetal heart reduces the accuracy of the following heartbeat calculation or can, at worst, lead to a recording of the maternal heart rate.

Starting point for this invention is the assumption that the different periodic signal sources are spatially separated. The invention intends to reduce the probability of recording an inaccurate or wrong heart rate caused by a superimposed Doppler signal by detecting the number of periodic signals, in particular caused by different sources, such as the heartbeat or (arterial/aortic) pulse of the fetus, the mother or a twin fetus, in a measurement path or, optionally, in a separate reference path, and subsequently adapting the duration of the time window and thereby adapting the ultrasonic detection volume.

Since maternal heart rate sources, such as the maternal artery, are mainly located behind the fetal heart rate sources, such as the fetal heart, a superimposition of the signals of the maternal heart rate sources with the signals of the fetal heart rate sources can be reduced or avoided by a reduction of the duration of the time window and thereby a reduction of the ultrasonic detection volume. The time window can for example be adapted, in particular reduced, for a defined time or until further ambiguous periodic signals, for example indicating the heart beat of the mother, disappear.

The method and device according to the invention have at least one of the following advantages:
- an improved ultrasound measurement,
- an improved ultrasound signal quality,
- an increased reliability and/or accuracy of a heart rate calculation,
- a signal segregation with manageable and affordable signal processing effort,
- the reduction of supervision and thereby the reduction of personal costs, and/or
- extreme body measurement can be performed, since the ultrasonic depth range is only reduced in the case of ambiguous periodic signals.

In the context of the present invention a received signal may also be a processed received signal, such as a received and amplified signal or a received, amplified and split signal part.

One run of steps a) to d) may comprise in particular several steps b) (and steps a)). Step c) may be performed on the basis of these steps b).

In the context of the present invention, the time window duration is in particular not adapted in the case of the assessment of one periodic signal. In the case of the assessment of no periodic signal, the window controller may maintain the time window, for example the original time window, or reset an adapted time window to the original time window. Preferably the original time window is set to cover the optimal depth range for the majority of pregnancies. For example, the original time window may be set to cover a depth range of about $\geq 3$ cm to about $\leq 25$ cm, for example of about $\geq 5$ cm to about $\leq 18$ cm.

In one embodiment the method comprises the steps of:
a) receiving an ultrasound signal reflected by a fetus;
b) demodulating the signal received in a time window with a specific duration;
c) assessing whether the time window contains more than one periodic signal; and
d) adapting the duration of the time window in the case of more than one assessed periodic signal;
wherein steps a) to d) are repeated with the adapted or non-adapted time window. This embodiment of the method according to the invention may be performed with a fetal cardiac monitoring device having no reference path or rather only one or more measurement paths. This has the advantage that a simple device is used.

In another embodiment the method comprises the steps of:
a) receiving an ultrasound signal reflected by a fetus and splitting the signal into at least one measurement path and at least one reference path;
b) demodulating one part of the signal received in a first time window with a specific duration in the measurement path and another part of the signal received in a second time window with a specific duration in the reference path;
c) assessing whether the second time window of the reference path contains more than one periodic signal; and
d) adapting the duration of the first time window of the measurement path in the case of more than one periodic signal assessed in the second time window of the reference path; wherein steps a) to d) are repeated with the adapted or non-adapted first time window. This embodiment of the method according to the invention may be performed with a fetal cardiac monitoring device having one or more measurement paths and one or more reference paths. This has the advantage that additional periodic signals are searched and eliminated in the back ground without interfering the measurement.

Preferably, in the measurement path and/or the reference path the signal is further split into two or more paths. Preferably, this is performed before or within step b). By this means, also further methods may be performed for improving the monitoring result, such as the method described in U.S. Pat. Nos. 4,984,576 and 5,170,791, whose entire disclosure is incorporated herewith by reference.

The first and second time window must not necessarily have the same duration, starting point and/or ending point. However, at the beginning of the method according to the invention the first and second time window may have the same duration, starting point and/or ending point.

In a further embodiment the second time window has a longer duration than the first time window.

By this means a broader depth range is screened by the second time window of the reference path, on which basis the first time window is adapted, whereby signal ambiguity is avoided in the first time window of the measurement path.

The second time window has a duration being, for example, up to about three times longer than the first time window duration. For example, the second time window has a duration of about 150 µs, whereas the first time window duration is shorter, for example the first time window duration is or is reduced to 50 µs. In particular, the second time window may have a fixed duration. In this connection, the first time window either has the same duration than the second time window at the beginning of the first loop of steps and gets shorter during the repeated loops of steps or the first time window has a shorter duration than the second time window already at the beginning of the first run of steps. In particular, the first and second time window may have the same starting point. For example, the first and second time window both have a starting point at about 140 µs (of the entire received time window, see FIGS. 1a and 1b).

In a further embodiment the duration of the time window is reduced in step d). By this means, further periodic signals may be excluded from the cardiac signal calculation, whereby the quality of the cardiac signal is improved.

In a further embodiment the duration of the time window is adapted, in particular reduced, in step d) by setting the ending point of the time window earlier. For example, at the beginning the first and second time window both have an ending point at about 290 µs, whereas the first time window is adapted, in particular reduced, by setting the ending point earlier, for example down to 190 µs (of the entire received time window, see FIGS. 1a and 1b). By this means, periodic signals caused by a distant source, such as a maternal artery, are excluded from the cardiac signal calculation, whereby the quality of the cardiac signal is improved.

In an embodiment, the duration of the time window is adapted, in particular reduced, in step d) stepwise. That is to say, in a first loop of the steps a) to d) the duration of the time window is reduced by a first step and in a second loop of the steps a) to d) the duration of the time window, which is already reduced by the first step, is further reduced by a second step, and so forth. This may be achieved by steps of successively diminishing size or by steps of fixed size.

In an embodiment, the adapted time window is maintained until the end of the measurement session. However, the fetus may change its position during the measurement session so that the ultrasound signal is no longer reflected by the fetus or rather the fetal heart and the periodic signal is lost.

In a further embodiment the adapted time window is therefore reset to the original time window in step d), if in the preceding step c) no periodic signal is assessed in the adapted time window. By this means, the depth of the detection range is broadened to regain a lost periodic signal.

In a further embodiment a fetal cardiac signal is calculated on the basis of at least one demodulated signal. The fetal cardiac signal is for example the heart rate, in particular the beat-to-beat heart rate. In the context of the present invention a demodulated signal may also be a processed demodulated signal, such as a demodulated and filtered signal, a demodulated, filtered and A/D converted signal or a demodulated, filtered, A/D converted and conditioned signal. In an embodiment, a fetal cardiac signal is calculated on the basis of the demodulation result of the measurement path or rather of the first time window.

In an embodiment, the calculation of the fetal cardiac signal is performed for the first time during the first run of the steps a) to d). However, it is also possible to perform the calculation of the fetal cardiac signal for the first time during a repeated loop of the steps a) to d). Since the steps a) to d) are repeated in a short time period, it is possible to output an adequate fetal cardiac signal in an acceptable time period even if the fetal cardiac signal is calculated for the first time during the first loop of the steps a) to d).

The method according to the invention may in particular be performed by a subsequently described ultrasonic fetal cardiac monitoring device according to the invention.

According to an embodiment, step a) is performed by an ultrasonic transducer, in particular by an ultrasonic transducer of the subsequently described ultrasonic fetal cardiac monitoring device according to the invention. In particular, step a) maybe performed by an ultrasonic Doppler transducer, whereby an ultrasound Doppler signal can be received in step a).

According to an embodiment, step b) is performed by a demodulator, in particular by a demodulator of the subsequently described ultrasonic fetal cardiac monitoring device according to the invention. In step b) a Doppler shifted signal may in particular be extracted from a carrier signal. For example, a pulsed signal with the same frequency as the carrier signal is therefore applied to one input of the demodulator. By this means, a synchronous demodulation is performed in step b).

According to an embodiment, step c) is performed by an ambiguity detector, in particular by an ambiguity detector of the subsequently described ultrasonic fetal cardiac monitoring device according to the invention. The periodic signal assessment may be performed in step c) by using a signal processing method, in particular for detecting periodic signals, for example selected from the group consisting of Fourier transformation, such as fast Fourier transformation, autocorrelation, peak search, wavelet transformation and combinations thereof. Here the signal processing method is combined with a classification method and/or counting and/or decision method. For example, peaks resulting from the signal processing method, such as fast Fourier transformation, are classified (overtone base frequency assignment) and the classified peaks are counted over time, wherein the time window is assessed to contain more than one periodic signal if the number of classified peaks in the time window exceeds a predefined threshold. The analysis window of step c) may then be longer than the analysis window for calculating the fetal cardiac signal. For example, the analysis window of step c) is about ≥4 s to about ≤8 s. Preferably, in step c) the periodic signal assessment is performed by using Fourier transformation and/or autocorrelation, in particular Fourier transformation, such as fast Fourier transformation.

According to an embodiment, step d) is performed by a window controller, in particular by a window controller of the subsequently described ultrasonic fetal cardiac monitoring device according to the invention.

Preferably, the fetal cardiac signal is calculated by a fetal cardiac signal calculator, in particular by a fetal cardiac signal calculator of the subsequently described ultrasonic fetal cardiac monitoring device according to the invention. The fetal cardiac signal may also be calculated by using a signal processing method, in particular for detecting periodic signals, for example selected from the group consisting of Fourier transformation, such as fast Fourier transformation, autocorrelation, peak search, wavelet transformation and combinations thereof. Here the signal processing method is also combined with a counting and/or decision method.

According to an embodiment, additionally, the method according to the invention comprises the step a0): amplifying the ultrasound signal received by the ultrasonic transducer. For example, the ultrasound signal received by the ultrasonic transducer is amplified in step a0), optionally split into a measurement path and reference path and subsequently demodulated in step b).

Furthermore, according to an embodiment, the method comprises the step b1): filtering at least one demodulated signal, for example for removing side bands and/or performing anti-aliasing filtering of the demodulated signal.

Moreover, according to an embodiment, the method comprises the step b2): analog to digital conversion of the demodulated signal. For example, the demodulated signal of step b) is filtered in step b1) and subsequently A/D converted.

In addition, according to an embodiment, the method comprises the step b3): conditioning the demodulated signal. Conditioning may comprise removing a DC offset, for example by high pass filtering, from the demodulated signal and/or rectifying the demodulated signal and/or smoothening the demodulated signal, for example by low pass filtering.

For further technical features and advantages of the method according to the invention reference is explicitly made to the explanations in the context of the subsequently described ultrasonic fetal cardiac monitoring device according to the invention, the Figures and description of the Figures.

Another object of the invention is an ultrasonic fetal cardiac monitoring device, comprising:

an ultrasonic transducer for generating an ultrasound signal and for receiving/transmitting an ultrasound signal reflected by a fetus, a demodulator for demodulating the received signal in at least one time window with a specific duration, an ambiguity detector for assessing whether at least one time window contains more than one periodic signal, a window controller for adapting the duration of at least one time window of the demodulator upon a signal from the ambiguity detector indicating more than one periodic signal, and a fetal cardiac signal calculator for calculating a fetal cardiac signal on the basis of at least one demodulated signal.

In particular, the device according to the invention may be adapted for performing the method according to the invention.

According to an embodiment, the ultrasonic transducer is an ultrasound Doppler transducer. The ultrasonic transducer may have an unfocused, approximately cylindrical ultrasound beam field. Preferably, the ultrasonic transducer comprises an array of piezo elements. In particular, the ultrasonic transducer may be designed for both generating/transmitting and receiving ultrasonic waves.

According to an embodiment, the demodulator is a demodulator for extracting a Doppler shifted signal from a carrier signal.

According to an embodiment, the fetal cardiac signal calculator is designed for calculating the fetal cardiac signal by using a signal processing method, in particular for detecting periodic signals, for example selected from the group consisting of Fourier transformation, such as fast Fourier transformation, autocorrelation, peak search, wavelet transformation and combinations thereof. Here, the signal processing method is combined with a counting and/or decision method.

According to an embodiment, the ambiguity detector additionally is designed for assessing whether at least one time window contains one periodic signal or no periodic signal. The ambiguity detector may in particular be designed for assessing periodic signals by using a signal processing method, in particular for detecting periodic signals, for example selected from the group consisting of Fourier transformation, such as fast Fourier transformation, autocorrelation, peak search, wavelet transformation and combinations thereof. Here, the signal processing method is combined with a classification method and/or counting method and/or decision method. For example, the ambiguity detector is designed for assessing periodic signals by classifying peaks (overtone base frequency assignment) resulting from the signal processing method, such as fast Fourier transformation, and counting the classified peaks over time, wherein if the number of classified peaks in the time window exceeds a predefined threshold, the time window is assessed to contain more than one periodic signal. In this connection, the analysis window of the ambiguity detector is longer than the analysis window of the fetal cardiac signal calculator. For example, the analysis window of the ambiguity detector is about ≥4 s to about ≤8 s. Preferably, the ambiguity detector is designed for assessing periodic signals by using Fourier transformation and/or autocorrelation, in particular Fourier transformation, such as fast Fourier transformation. Furthermore, according to an embodiment, the ambiguity detector is designed for transmitting a signal indicating more than one periodic signal to the window controller. Additionally the ambiguity detector may be designed for transmitting a signal indicating one periodic signal or no periodic signal to the window controller.

According to an embodiment, the window controller is designed for adapting, in particular reducing, the duration of at least one time window, in the case of a signal from the ambiguity detector indicating more than one periodic signal. Said window controller is in particular designed for adapting the duration of at least one time window by setting the ending point of the time window earlier. Furthermore, the window controller may be designed for not adapting the duration of at least one time window upon a signal from the ambiguity detector indicating one periodic signal. Moreover, according to an embodiment, the window controller is designed for maintaining the time window, for example the original time window, or resetting an adapted time window to the original time window upon a signal from the ambiguity detector indicating no periodic signal.

In one embodiment the device comprises an amplifier for amplifying the ultrasound signal received by the ultrasonic transducer.

In another embodiment the device comprises at least one filter, in particular for removing side bands and/or performing anti-aliasing filtering of the demodulated signal. For example, the device comprises at least one band filter, in particular with cut off frequencies at 100 Hz and 500 Hz.

In a further embodiment the device comprises an analog to digital converter for converting the demodulated signal.

In yet another embodiment the device comprises a signal conditioner for conditioning the demodulated signal. In particular, the signal conditioner may be designed for conditioning the demodulated signal by removing a DC offset, for example by high pass filtering, from the demodulated signal and/or by rectifying the demodulated signal and/or by smoothening the demodulated signal, for example by low pass filtering.

In a further embodiment the ambiguity detector and the fetal cardiac signal calculator are both connected to the signal conditioner, wherein the ambiguity detector is connected by the window controller to the demodulator.

In another embodiment the device comprises at least one demodulator-filter-converter-conditioner arrangement, wherein a demodulator for demodulating the received signal in at least one time window with a specific duration is connected to at least one filter, in particular for removing side bands and/or performing anti-aliasing filtering of the demodulated signal, wherein the filter is connected to an analog to digital converter for converting the demodulated signal, and wherein the analog to digital converter is connected to a signal conditioner for conditioning the demodulated signal. Here, the ambiguity detector and the fetal cardiac signal calculator are both connected to the signal conditioner of the demodulator-filter-converter-conditioner arrangement, wherein the ambiguity detector is connected by the window controller to the demodulator.

In a further embodiment the device comprises a signal splitter for splitting the received signal into a measurement path and a reference path. Here, the measurement path and the reference path both comprise a demodulator and a signal conditioner connected (directly or indirectly) to the demodulator. In particular, the measurement path and the reference path may both comprise a demodulator-filter-converter-conditioner arrangement. The fetal cardiac signal calculator may be connected to the signal conditioner of the measurement path. The ambiguity detector may be connected to the signal conditioner of the reference path. The ambiguity detector may additionally be connected by the window controller to the demodulator of the measurement path. In this embodiment further periodic signals are searched and eliminated in the background without interfering with the measurement path. Furthermore, in this embodiment the time window assessed by the ambiguity detector may have a longer duration than the time window of the demodulated signal processed by the fetal cardiac signal calculator for calculating the fetal cardiac signal, since the ambiguity detector and the fetal cardiac signal calculator belong to different paths. The time window assessed by the ambiguity detector for instance has a duration being, for example, up to about three times longer than the duration of the time window of the demodulated signal processed by the fetal cardiac signal calculator. For example, the time window assessed by the ambiguity detector has a duration of about 150 µs, whereas the duration of the time window of the demodulated signal processed by the fetal cardiac signal calculator is shorter, for example the duration of the first time window is or is reduced to 50 µs. The ambiguity detector may be designed for assessing a time window of a fixed duration. In particular, the time window assessed by the ambiguity detector and the time window of the demodulated signal processed by the fetal cardiac signal calculator may have the same starting point, for example, the first and second time window both have a starting point at about 140 µs (of the entire received time window, see FIGS. 1a and 1b).

Additionally, according to an embodiment, the device comprises at least one measurement and/or reference path splitter for splitting the signal of the measurement path or reference path into two or more paths.

For further technical features and advantages of the device according to the invention reference is explicitly made to the explanations in the context of the method of fetal cardiac monitoring according to the invention, the Figures and description of the Figures.

Another object of the invention is a computer program enabling a processor to carry out the method according to the invention.

A further object of the present invention is a cardio toco graph (CTG) comprising an ultrasonic fetal cardiac monitoring device according to the invention or performing a method of fetal cardiac monitoring according to the invention.

These and other aspects of the invention will be apparent from and elucidated with reference to the embodiments described hereinafter.

DETAILED DESCRIPTION OF THE DRAWINGS

Figure 1A:
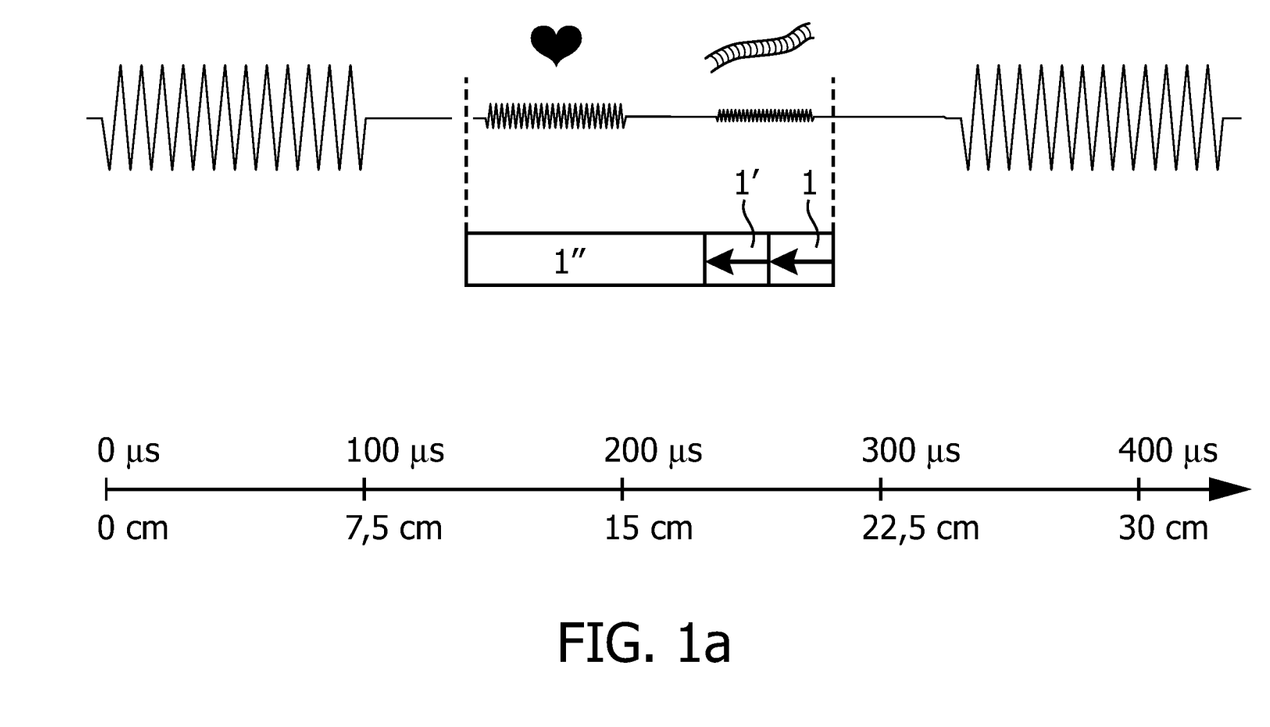
FIG. 1a is a schematic diagram illustrating one embodiment of the method and device according to the invention with a measurement path but without reference path.

FIG. 1a is a schematic diagram illustrating one embodiment of the method and device according to the invention with a measurement path but without a reference path. The relationship between the depth position of the fetal heart (indicated by a heart icon), the maternal abdominal artery (indicated by an artery icon), the received ultrasound signal and the demodulation time window 1,1',1" is shown in FIG. 1. In particular, FIG. 1a illustrates that besides the fetal heart also the pulsation of the maternal abdominal artery generates an ultrasound reflection and causes a periodic signal in the time window.

As long as the strength of the unwanted periodic signal (maternal abdominal artery) is below a certain level, the influence of the unwanted periodic signal may be reduced by subsequent signal processing. However, depending on various, time-variable factors characterizing the strength of the reflected ultrasound echo, the components of the ultrasound signal may change unpredictably. Situations with amplitude equality between the fetal signal and the interfering maternal signal may occur. Due to signal superposition the real peak position of the fetal heart beat may be blurred, which subsequently may lead to an inaccurate heart rate. Episodes with strong fetal/maternal signal superposition often show a reduction or an increase of the calculated heart rate, which are sometimes interpreted as a deceleration or acceleration, respectively. Depending on the intensity of the unwanted maternal heartbeat, this signal even drowns out the fetal signal fraction. Heart rate alterations caused by maternal and fetal signal interaction are retrospectively difficult to identify and may at worst lead to a misinterpretation. Misinterpreting a wrong heart rate trace may lead to unnecessary interventions or surgery, or to failure to detect fetal distress. To avoid wrongly recorded fetal heart rate values, up to now permanent supervision of the recorded heart rate and if necessary manual interaction for transducer repositioning is required. Therefore, the likelihood of recording a wrong heart rate is relatively high. Unfortunately, up to now, no practical method has been disclosed which allows signal segregation by means of a manageable and affordable signal processing effort.

Figure 1B:
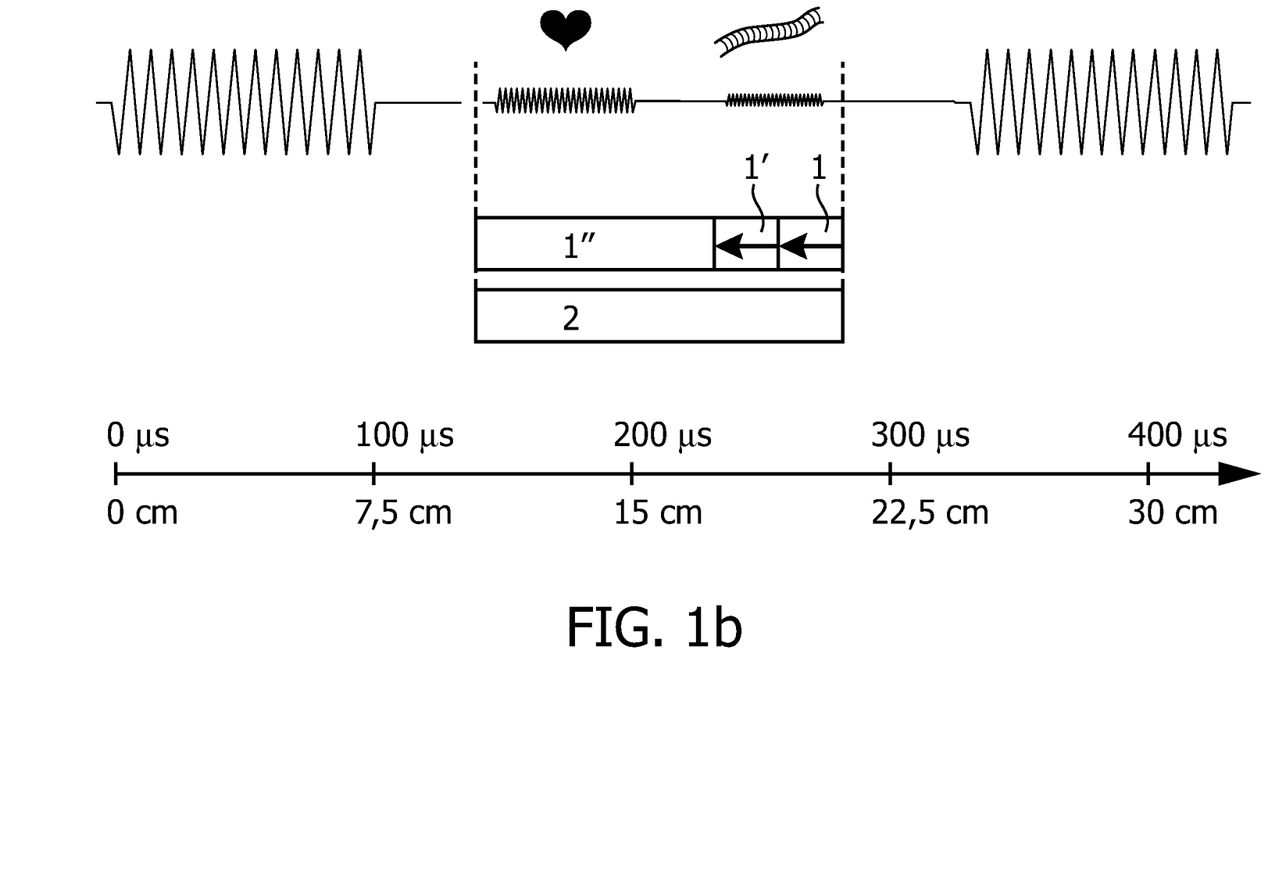
FIG. 1b is a schematic diagram illustrating another embodiment of the method and device according to the invention with a measurement path and with a reference path.

Since periodic signal contribution other than the reflection from the fetal heart reduces the accuracy of the following heart beat calculation or may, at worst, lead to recording of the maternal heart rate, it is the basic idea of the invention to reduce or avoid periodic signals other than those of the fetus in the demodulation time window 1,1',1" from which the fetal cardiac signal is calculated (measurement path). FIG. 1 shows that the fetal signal (indicated by the heart icon) occurs earlier in the demodulation time window 1,1',1" than the maternal signal (indicated by the artery icon). According to the invention, superimposition of the fetal and maternal signal is reduced or avoided by adapting, in particular reducing, the duration of the demodulation time window 1,1',1" from which the fetal cardiac signal is calculated. As illustrated in FIG. 1b the reduction of the demodulation time window duration 1,1',1" may be sufficient to eliminate the influence of the maternal interference source.

Since it is not necessary to reduce the duration of the demodulation time window 1,1',1", if no periodic signal other than the fetal periodic signal is present and an unnecessary reduction of the duration of the demodulation time window 1,1',1" could bring forth a signal loss of the fetal signal, the method according to the invention comprises step c) which checks if there is more than one periodic signal in a demodulation time window 1,1',1". In the subsequent step d) of the method according to the present invention, the duration of the demodulation time window 1,1',1", from which the fetal cardiac signal is calculated, is adapted if more than one periodic signal was assessed in step c). If in step c) only one periodic signal was assessed in a demodulation time window, the duration of the demodulation time window 1,1',1" from which the fetal cardiac signal is calculated is in particular not adapted or rather can be maintained.

FIG. 1a illustrates that the duration of the demodulation time window 1,1',1" may be adapted by advancing the ending point of the demodulation time window 1,1',1", that is to say by setting the ending point of the demodulation time window 1,1',1" at an earlier point in time than before. This has also the effect that the duration of the demodulation time window 1,1',1" is reduced. Moreover FIG. 1a shows that the starting point of the demodulation time window 1,1',1" may be unchanged.

After step d) of the first run of steps a) to d), the steps of the method are repeated with the adapted demodulation time window 1' (in case of more than one periodic signal) or with the non-adapted demodulation time window 1 (such as in the case of one periodic signal in the time window of the previous step c)).

If in step c) of the subsequent loop of steps a) to d) still more than one periodic signal is detected in the adapted demodulation time window 1', the duration of the adapted demodulation time window 1' is further adapted in step d), while the method steps a) to d) are then repeated with the twice adapted demodulation time window 1" as illustrated by FIG. 1a.

In the example of FIG. 1a, only one periodic signal indicating the fetal signal will be assessed in the twice adapted demodulation window 1" in step c) of the following loop of steps a) to d). Therefore, in step d) of this step loop, the duration of the demodulation time window 1" will not be further adapted and the following step loops will be performed with the twice adapted demodulation time window 1". If the fetal periodic signal should get lost later on, the twice adapted time window 1" can be reset to the original time window 1.

In the example of FIG. 1, the adaption of the demodulation window 1,1',1" is performed by fixed steps (steps of the same size). However, in the context of the present invention it is also possible to perform the adaption in steps, whose size is set successively smaller.

FIG. 1b is a schematic diagram illustrating another embodiment of the method and device according to the invention with a measurement path and with a reference path. The embodiment shown in FIG. 1b differs in essence from the embodiment shown in FIG. 1a in the following respect: the received signal is split into a measurement path and a reference path (step a). In step b) one part of the signal received in a first time window 1,1',1" in the measurement path and another part of the signal received in a second time window 2 in the reference path are demodulated. Thereby it is assessed whether the second time window 2 of the reference path contains more than one periodic signal. In the case that more than one periodic signal is assessed in the second time window 2 of the reference path, the duration of the first time window 1,1',1" of the measurement path is adapted. In other words, in this embodiment the periodic signal assessment of step c) (reference path) and the demodulation time window adaption of step d) (measurement path) are performed in different signal paths, whereby the steps a) to d) are repeated with the adapted first time window 1',1" or non-adapted first time window 1. The second time window 2 may remain unchanged. This embodiment has the advantage that additional periodic signals may be searched and eliminated in the background without interfering with the measurement.

As illustrated by FIG. 1b, the demodulation time windows 1,2 of the measurement path and the reference path may have the same duration at the beginning, but the duration of the demodulation time window 1,1',1" may be reduced during the measurement. However, at the beginning, the first demodulation time window 1 may also have a shorter duration than the second demodulation window 2 (not illustrated). In particular, the duration of the first demodulation time window 1 may be much smaller than the duration of the second demodulation time window 2.

Figure 2A:
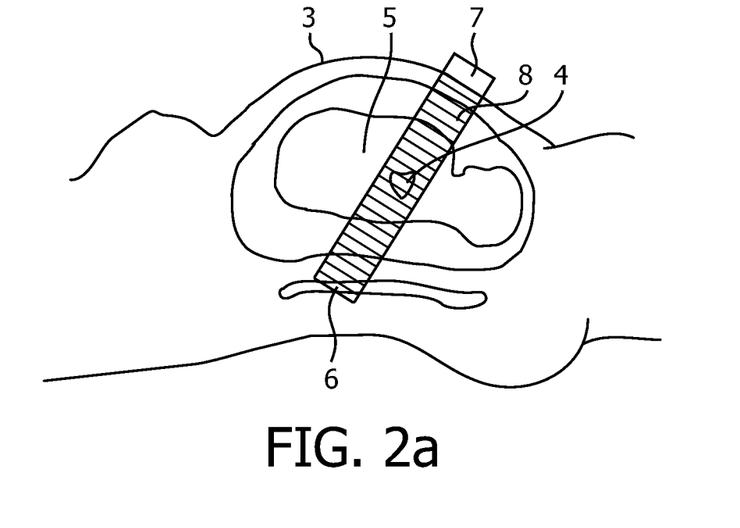
FIGS. 2a and 2b are schematic cross-sectional views of a pregnant woman during fetal cardiac monitoring.
Figure 2B:
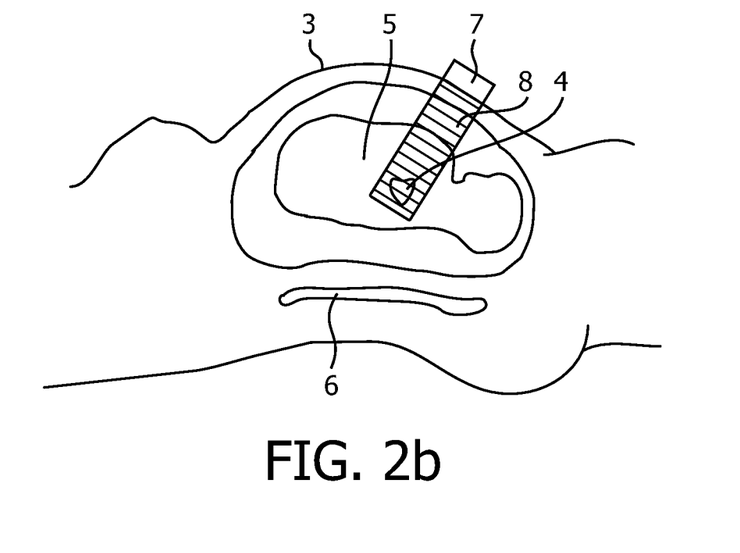

FIGS. 2a and 2b are schematic cross-sectional views of a pregnant woman 3 during fetal cardiac monitoring. FIGS. 2a and 2b illustrate the spatial separation of the heart 4 of the fetus 5 and the maternal abdominal artery 6. Furthermore, FIGS. 2a and 2b show that by a reduction of the demodulation time window the depth of the detection volume 8 of an ultrasonic fetal cardiac monitoring device 7 placed on the abdomen of the pregnant woman 3 is reduced so that the periodic signal of the maternal abdominal artery 6 does not superimpose with the periodic signal of the heart 4 of the fetus 5 used for calculating a fetal cardiac signal, such as the beat-to-beat heart rate.

Figure 3A:
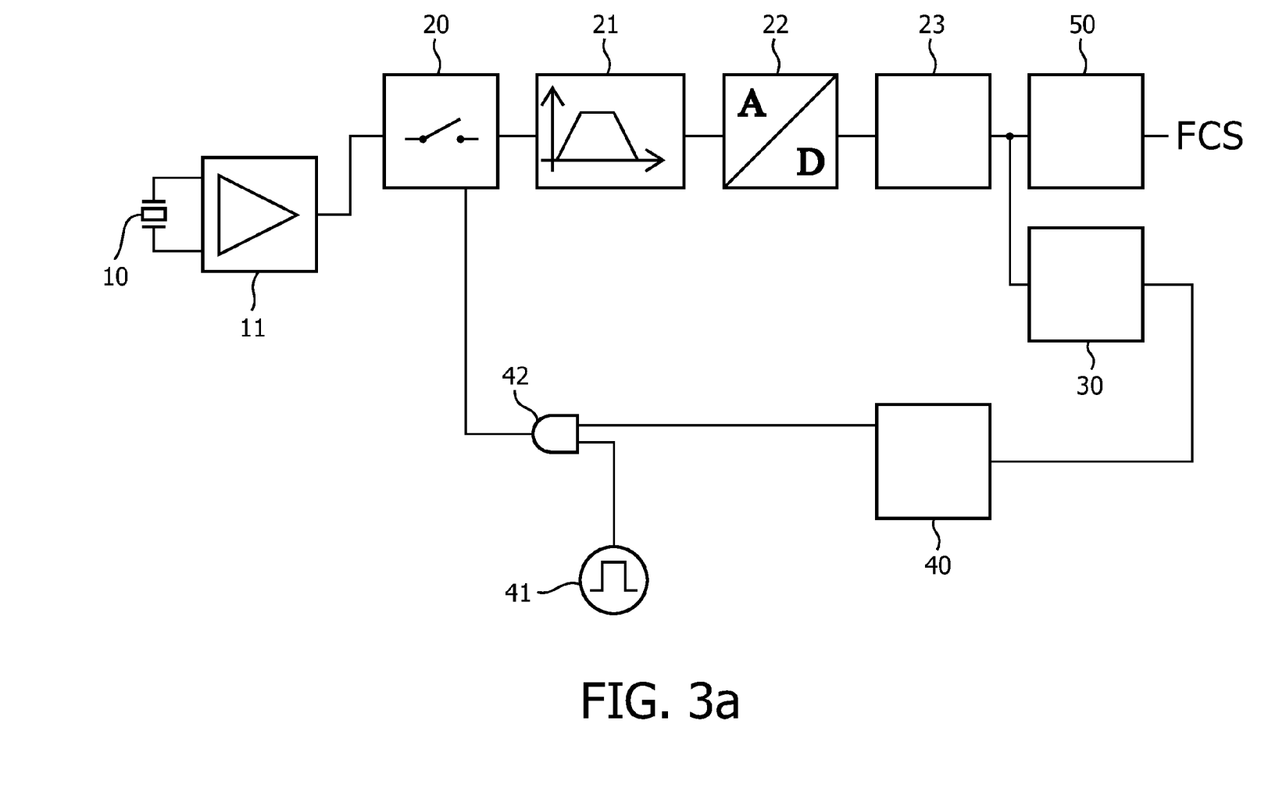
FIG. 3a is a block diagram illustrating another embodiment of the method and device according to the invention with a measurement path but without reference path.

FIG. 3a is a block diagram illustrating another embodiment of the method and device according to the invention with a measurement path but without a reference path. FIG. 3a shows an ultrasonic fetal cardiac monitoring device comprising an ultrasonic transducer 10 for generating an ultrasound signal and for receiving an ultrasound signal reflected by a fetus, a demodulator 20 for demodulating the received signal in at least one time window with a specific duration, an ambiguity detector 30 for assessing whether at least one time window contains more than one periodic signal, a window controller 40 for adapting the duration of at least one time window of the demodulator 20 upon a signal from the ambiguity detector 30 indicating more than one periodic signal, and a fetal cardiac signal calculator 50 for calculating a fetal cardiac signal (FCS) on the basis of at least one demodulated signal.

FIG. 3a illustrates that the device further comprises an amplifier 11 for amplifying the ultrasound signal received by the ultrasonic transducer 10. This amplified, received signal is transmitted from the amplifier 11 to the demodulator 20. FIG. 3a further shows that the device comprises a filter 21 for removing sidebands and performing anti-aliasing filtering of the demodulated signal of the demodulator 20. Moreover, FIG. 3a shows that the device comprises an analog to digital converter 22 for converting the demodulated and filtered signal of the filter 21. Further on, FIG. 3a illustrates that the device comprises a signal conditioner 23 for conditioning the demodulated, filtered and A/D converted signal of the analog to digital converter 22.

FIG. 3a shows that the ambiguity detector 30 and the cardiac signal calculator 50 are both connected to the signal conditioner 23, wherein the ambiguity detector 30 is connected by the window controller 40 and a gate 42, which is connected to a demodulation clock 41, to the demodulator 10.

Figure 3B:
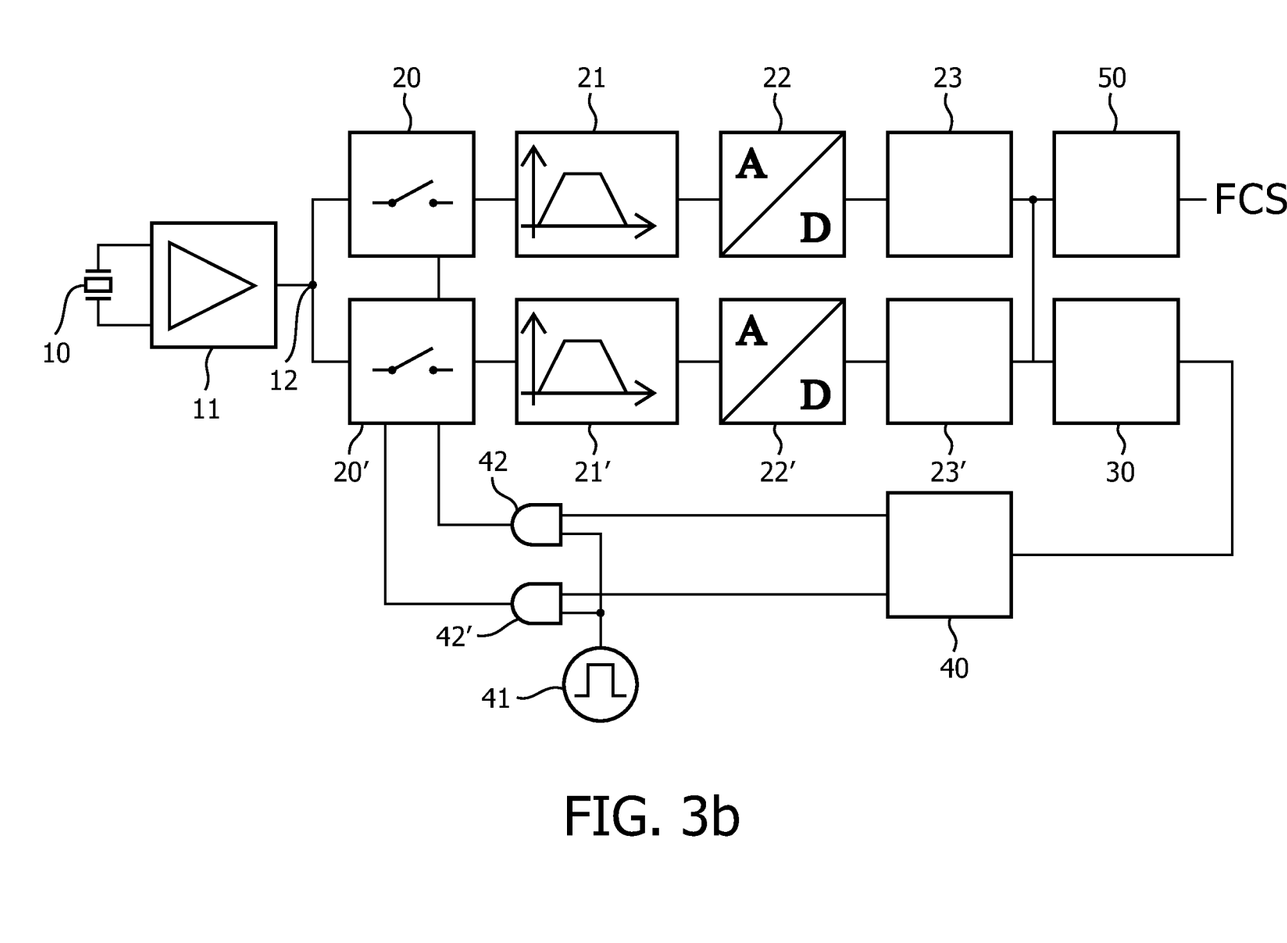
FIG. 3b is a block diagram illustrating another embodiment of the method and device according to the invention with a measurement path and with a reference path.

FIG. 3b is a block diagram illustrating another embodiment of the method and device according to the invention with a measurement path and a reference path. The embodiment shown in FIG. 3b differs in essence from the embodiment shown in FIG. 3a in that the device comprises a signal splitter 12 for splitting the received signal into a measurement path (upper path) and a reference path (lower path). Here, the measurement path and the reference path both comprise a demodulator 20,20', a filter 21,21' connected to the demodulator 20,20', an analog to digital converter 22,22' connected to the filter 21,21' and a signal conditioner 23,23' connected to the analog to digital converter 22,22'. FIG. 3b illustrates that the fetal cardiac signal calculator 50 is connected to the signal conditioner 23 of the measurement path, while the ambiguity detector 30 is connected to the signal conditioner 23' of the reference path and via the window controller 40 and gates 42,42', which gates are connected to a demodulation clock 41, to the demodulator 20 of the measurement path.

In the embodiments shown in FIGS. 3a and 3b the ultrasonic transducer 10 may be a piezo element array, which is repetitively excited in order to generate ultrasonic wave packets, which travel towards the fetal heart during the transmission phase. These traveling wave packets are reflected and frequency shifted due to the Doppler effect on various moving layers in the body of the pregnant woman and the fetus, for example from the fetal heart and a maternal artery. Since the fetal heart and the maternal artery are at different distances relative to the surface of the transducer, the wave packets require different traveling times down to the point of reflection and back to the transducer.

The piezo element array 10 may be used in both directions. When transmission has finished, the transducer 10 switches from transmit to receive mode. After amplification by the amplifier 11 the received signal is optionally split into two signal paths, i.e. the reference path and the measurement path. Both signal paths may be completely identical for the first three stages of signal processing.

In the simpler embodiment without reference path shown in FIG. 3a, the signal for the ambiguity detector 30 originates from the signal conditioner 23 of the measurement path. By combining a measurement path and a reference path the efficiency of the implementation of the ambiguity detection is enhanced.

With or without a separate reference path, the signal in particular first passes the demodulation stage. The demodulator 20,20' extracts the Doppler shifted signal from the carrier signal. For demodulating the Doppler shifted signal, a pulsed signal with exactly the same frequency is applied as the carrier signal to the input of the demodulator/s 20,20' (synchronous demodulation). The duration of the pulsed signal is controlled by the window controller 40. As explained above, the reference path and the measurement path must not necessarily have the same duration and starting point of the demodulation signal in the context of the present invention.

Preferably, the band filter 21,21' has cut off frequencies at 100 Hz and 500 Hz, removes sidebands and performs an anti-aliasing filtering. After analog to digital conversion by the analog to digital converter 22,22' the raw signal passes the signal conditioner 23,23' where the signal may be high pass filtered to remove the DC offset, rectified and low pass filtered for smoothening.

Finally, the fetal cardiac signal calculator 50 of the measurement path may calculate the heart rate by using for example Fourier transformation or autocorrelation and a subsequent scoring and decision unit.

Depending on the embodiment, either the output of the signal conditioner 23,23' of the measurement path or the reference path is further processed in the ambiguity detector 30. Ambiguity detection may in particular be done by fast Fourier transformation (FFT) processing of the pre-processed signal. However, other methods like autocorrelation may also be used. In order to reduce the artifact sensitivity, the fast Fourier transformation is calculated over a longer time frame, for example of about 4 s to 8 s. Pure signals from one single source will show one peak at the base frequency and additional peaks at multiples of the base frequency. With signals from two sources having different frequencies, such as the fetal heart and maternal artery, two peaks and their multiples are visible in the frequency domain. For ambiguity detection the peaks are classified and counted over time. If the number of ambiguous peaks within a certain time reaches a predefined threshold, a signal to the window control unit 40 may force the change of at least the demodulation time window of the measurement path. Assuming that the demodulation time window of the measurement path was at its maximum, the depth range may cover the signal sum of the fetal heart and the maternal artery.

Forced by the ambiguity signal the demodulation time window may then be reduced by a certain value. Consequently the reduction of the maximum reach of the ultrasound beam is proportional. The reduction of the demodulation time window duration may be maintained for the entire duration of the measurement session. A reset to full depth is for example coupled to the detection of signal loss or, depending on the presence of an independent reference path, to the disappearance of an ambiguous signal.

If no reference channel is available, the reduction of the demodulation time window duration may be done by a fixed step or in a loop where the window duration is reduced in small steps with a subsequent check if the ambiguity disappears.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method of fetal cardiac monitoring, comprising the steps of:
   a) receiving an ultrasound signal reflected by a fetus;
   b) demodulating the signal received in at least one time window with a specific duration;
   c) assessing whether at least one time window contains more than one periodic signal; and
   d) reducing the duration of at least one time window in the case of more than one assessed periodic signal to generate an adapted time window;
   wherein steps a) to d) are repeated until step c) assesses the adapted time window to have only one periodic signal.

2. The method according to claim 1, further comprising: e) calculating a fetal cardiac signal on the basis of the demodulated signal from the adapted time window having only one periodic signal.

3. The method according to claim 1, wherein in step d) the duration of the time window is reduced by setting the ending point of the time window earlier.

4. The method according to claim 1, wherein the adapted time window is reset to the original time window in step d), if in the preceding step c) no periodic signal is assessed in the adapted time window.

5. A non-transitory computer program enabling a processor to carry out the method of claim 1.

6. A method of fetal cardiac monitoring, comprising the steps of:
   a) receiving an ultrasound signal reflected by a fetus and splitting the signal into at least one measurement path and at least one reference path;
   b) demodulating one part of the signal received in a first time window with a specific duration in the measurement path and another part of the signal received in a second time window with a specific duration in the reference path;
   c) assessing whether the second time window of the reference path contains more than one periodic signal; and
   d) adapting the duration of the first time window of the measurement path in the case of more than one periodic signal assessed in the second time window of the reference path; and
   wherein steps a) to d) are repeated with the adapted or non-adapted first time window.

7. The method according to claim 6, wherein the second time window has a longer duration than the first time window.

8. An ultrasonic fetal cardiac monitoring device, comprising:
   an ultrasonic transducer for generating an ultrasound signal and for collecting an ultrasound signal reflected by a fetus; and
   one or more processors electrically connected to the ultrasonic transducer, and configured for:
      receiving a signal from the ultrasonic transducer;
      demodulating the received signal in at least one time window with a specific duration;
      assessing whether at least one time window contains more than one periodic signal; and
      reducing the duration of at least one time window in the case of more than one assessed periodic signal to generate an adapted time window;
      wherein the receiving, the demodulating, the assessing and the reducing are repeated until it is assessed that the adapted time window has only one periodic signal.

9. The device according to claim 8, wherein the device comprises an amplifier for amplifying the ultrasound signal collected by the ultrasonic transducer.

10. The device according to claim 8, wherein the device comprises at least one filter.

11. The device according to claim 8, wherein the device comprises an analog to digital converter for converting the demodulated signal.

12. The device according to claim 8, wherein the device comprises a signal conditioner for conditioning the demodulated signal.

13. The device according to claim 8, wherein an ambiguity detector and a cardiac signal calculator are both connected to a signal conditioner, wherein the ambiguity detector is connected by a window controller to a demodulator.

14. An ultrasonic fetal cardiac monitoring device, comprising:
   an ultrasonic transducer for generating an ultrasound signal and for receiving an ultrasound signal reflected by a fetus,
   a demodulator for demodulating the received signal in at least one time window with a specific duration,
   an ambiguity detector for assessing whether at least one time window contains more than one periodic signal,
   a window controller for adapting the duration of at least one time window of the demodulator upon a signal from the ambiguity detector indicating more than one periodic signal, and
   a fetal cardiac signal calculator for calculating a fetal cardiac signal on the basis of at least one demodulated signal,
   wherein the device comprises a signal splitter for splitting the received signal into a measurement path and a reference path, wherein both the measurement path and the reference path comprise a demodulator and a signal conditioner connected to the demodulator, wherein the fetal cardiac signal calculator is connected to the signal conditioner of the measurement path, and wherein the ambiguity detector is connected to the signal conditioner of the reference path and via the window controller to the demodulator of the measurement path.

* * * * *